United States Patent
Utada et al.

(10) Patent No.: US 10,233,487 B2
(45) Date of Patent: Mar. 19, 2019

(54) USE OF GEL BEADS TO CONTROL DROPLET DISPERSION

(71) Applicant: Bio-Rad Laboratories, Inc., Hercules, CA (US)

(72) Inventors: Andrew Utada, Hercules, CA (US); Jeremy Agresti, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 48 days.

(21) Appl. No.: 15/467,282

(22) Filed: Mar. 23, 2017

(65) Prior Publication Data

US 2017/0275679 A1    Sep. 28, 2017

Related U.S. Application Data

(60) Provisional application No. 62/312,650, filed on Mar. 24, 2016.

(51) Int. Cl.
| | | |
|---|---|---|
| *C12Q 1/6834* | (2018.01) | |
| *C08J 3/12* | (2006.01) | |
| *C12Q 1/6806* | (2018.01) | |
| *C12Q 1/6844* | (2018.01) | |
| *G01N 33/58* | (2006.01) | |

(52) U.S. Cl.
CPC .......... *C12Q 1/6834* (2013.01); *C08J 3/126* (2013.01); *C12Q 1/6806* (2013.01); *C12Q 1/6844* (2013.01); *G01N 33/585* (2013.01); *C08J 2300/00* (2013.01)

(58) Field of Classification Search
CPC ........................... C12Q 1/6834; G01N 33/585
See application file for complete search history.

(56) References Cited

U.S. PATENT DOCUMENTS

| | | | |
|---|---|---|---|
| 4,798,721 A | 1/1989 | Yahagi et al. | |
| 4,971,833 A * | 11/1990 | Larsson | B01J 20/3274 210/635 |
| 6,126,936 A | 10/2000 | Lanza | |
| 7,022,473 B1 * | 4/2006 | Tanga | C12Q 1/6834 435/283.1 |
| 2002/0085987 A1 | 7/2002 | Brown et al. | |

(Continued)

FOREIGN PATENT DOCUMENTS

| | | |
|---|---|---|
| WO | 2012/015744 A2 | 10/2000 |
| WO | WO 2014028537 * | 2/2014 |

OTHER PUBLICATIONS

Seiffert, Microgel Capsules Tailored by Droplet-Based Microfluidics, 2013, ChemPhysChem, 14, 295-304. (Year: 2013).*

(Continued)

*Primary Examiner* — Narayan K Bhat
(74) *Attorney, Agent, or Firm* — Kilpatrick Townsend and Stockton LLP

(57) ABSTRACT

A method of generating deformable gel beads that contain a single colloidal particle is described. Gel beads containing a particle are isolated from those that do not contain a particle, based on differences between the buoyant density of these gel bead populations. The gel beads containing a particle are subsequently co-encapsulated at a high efficiency into droplets that can comprise additional objects such as cells, other particles, or reagents. The gel coating on the rigid particle prevents clogging in narrow channels, such as those of a droplet generator.

17 Claims, 3 Drawing Sheets

(56) References Cited

U.S. PATENT DOCUMENTS

| | | |
|---|---|---|
| 2005/0112655 A1 | 5/2005 | Banerjee et al. |
| 2009/0012187 A1 | 1/2009 | Chu et al. |
| 2011/0018153 A1* | 1/2011 | Lihme .................... B01J 13/046 264/8 |
| 2012/0295026 A1 | 11/2012 | Courtois et al. |

OTHER PUBLICATIONS

PCT/US2017/023765, "International Search Report and Written Opinion", dated Jun. 15, 2017, 13 pages.

\* cited by examiner

USE OF GEL BEADS TO CONTROL DROPLET DISPERSION

CROSS-REFERENCES TO RELATED APPLICATIONS

This application claims the benefit of U.S. Provisional Application No. 62/312,650, filed Mar. 24, 2016, which is incorporated in its entirety herein for all purposes

BACKGROUND OF THE INVENTION

Droplet-based technology is a tool with promising applications in the fields of biology, biotechnology, computation, and chemical analysis. In this technology, droplets are formed within an inert and immiscible carrier fluid or continuous phase at rates of several kHz using microfluidic techniques and devices. Once formed, these droplets can then be combined, split, and selected in any number of downstream steps. The speed, small volumes, and discrete partitioning that are characteristic of the technology have proven useful in many areas, such as those involving analyzing genetic material, screening large libraries of chemical compounds, and evolving cells and enzymes.

One application of this technique involves the encapsulation of individual cells within picoliter-scale monodisperse droplets. This enables the quantitative experimentation of large cell populations on a single-cell basis. Another application can be found in Droplet Digital PCR, in which the polymerase chain reaction samples are diluted and partitioned into a plurality of different reactions, such that each reaction contains at most one copy of the target nucleotide sequence to be amplified. As a result, a determination can be made of the original copy number of a DNA molecule by counting the number of reactions in which a successful PCR amplification occurs. Further applications and devices for droplet-based technologies are discussed in Koster S, Angile F E, Duan Agresti J J, Wintner A, Schmitz C, Rowat A C, Merten C A, Pisignano D, Griffiths A D, and Weitz D A. Drop-based microfluidic devices for encapsulation of single cells. Lab on a Chip 2008; 8: 1110, which is entirely incorporated herein by reference for all purposes.

One of the primary challenges with these techniques and applications is the variability in distribution of material among the discrete droplets. Because the distribution is essentially random, droplets can be formed that contain a higher or smaller amount of material than desired. For example, in applications requiring one particle per droplet, significant percentages of the droplet population generated may instead contain multiple particles or no particles at all.

A proposed solution, described in Edd J F, Di Carlo D, Humphry K J, Koster S, Irimia D, Weitz D A, and Toner M. Controlled encapsulation of single-cells into monodisperse picoliter droplets. Lab on a Chip 2008; 74: 61402, which is entirely incorporated herein by reference for all purposes, is to regulate the flow of cells entering a droplet generating device. This regulation is such that the cells are evenly spaced with one another, and that they enter the droplet generator at a frequency that precisely matches that of droplet formation.

An alternate solution, described in Abate A R, Chen C-H, Agresti, J J, and Weitz D A. Beating Poisson encapsulation statistics using close-packed ordering. Lab on a Chip 2009; 9: 2628-2631, which is entirely incorporated herein by reference for all purposes, is to use deformable particles that are closely packed. These particles comprise a compliant gel that has enough flexibility in its structure to prevent clogging of channels. In this way, the volume fraction of the particles can be increased beyond what would otherwise be practical, and the resulting efficiency of particle encapsulation can be increased.

BRIEF SUMMARY OF THE INVENTION

Provided herein is a method for generating a population of gel-coated particles. In some embodiments, the method comprising providing a plurality (e.g., at least 100; 200; 300; 500; 750; 1000; 2500; 5000; 7500; 10,000; 15,000; 20,000; 30,000; 50,000; 75,000; 100,000; 250,000; 500,000; $1 \times 10^6$ or more)) of particles, and coating the particles with a gel to generate a starting mixture of gel-coated particles and gel beads lacking the particles, wherein the density of the gel-coated particles is higher than the density of the gel beads. In some embodiments, the method further comprises allowing the mixture to settle in a fluid such that a majority of the gel-coated particles separate in the fluid to a lower position than a majority of the gel beads. In some embodiments, the method further comprises collecting the gel-coated particles without a majority of the gel beads, thereby generating a collected population of gel-coated particles. In some embodiments, some gel-coated particles comprise multiple particles within one gel In some embodiments, the particles of the method can comprise polymethylmethacrylate, glass, polystyrene, or other polymers compatible with solid-phase oligonucleotide synthesis. In some embodiments, the particles of the method can have diameters in the range from about 1 μm to about 60 μm. In some embodiments of the method, oligonucleotides are linked to the particles. In some embodiments, each of a majority of the particles of the method can be linked to a different oligonucleotide, wherein the sequences of the different oligonucleotides are distinguishable from one another.

In some embodiments, the gel of the method can be selected from the group consisting of polyacrylamide, agarose, agar, PLGA, polyethylene glycol, or alginate. In some embodiments, the gel beads lacking particles can have diameters in the range from about 10 μm to about 100 μm.

In some embodiments, the starting mixture generated by the coating of the method can have at least 10, 15, 20, or more gel beads lacking the particles per gel-coated particle.

In some embodiments, the fluid of the method can be a mixture of two immiscible fluids. In some embodiments, the two immiscible fluids are an aqueous fluid and an oil.

In some embodiments, the method further comprises inserting gel-coated particles from the collected population of gel-coated particles into droplets.

Also provided is a mixture of gel-coated particles and gel beads lacking the particles, wherein the density of the gel-coated particles is higher than the density of the gel beads, and the mixture has at least 10 gel-coated particles per gel bead lacking the particles. In some embodiments, the mixture comprises at least 100; 200; 300; 500; 750; 1000; 2500; 5000; 7500; 10,000; 15,000; 20,000; 30,000; 50,000; 75,000; 100,000; 50,000; 500,000; $1 \times 10^6$ or more gel-coated particles.

In some embodiments, the particles of the mixture can comprise polymethylmethacrylate, glass, polystyrene, or other polymers compatible with solid-phase oligonucleotide synthesis. In some embodiments, the particles of the mixture can have diameters in the range from about 1 μm to about 60 μm. In some embodiments, oligonucleotides are linked to the particles. In some embodiments, each of a majority of the particles of the mixture can be linked to a different oligonucleotide, wherein the sequences of the different oligonucleotides are distinguishable from one another.

In some embodiments, the gel of the mixture can be selected from the group consisting of polyacrylamide, agarose, agar, PLGA, polyethylene glycol, or alginate. In some embodiments, the gel beads lacking particles of the method can have diameters in the range from about 10 μm to about 100 μm.

DEFINITIONS

Figure 1:
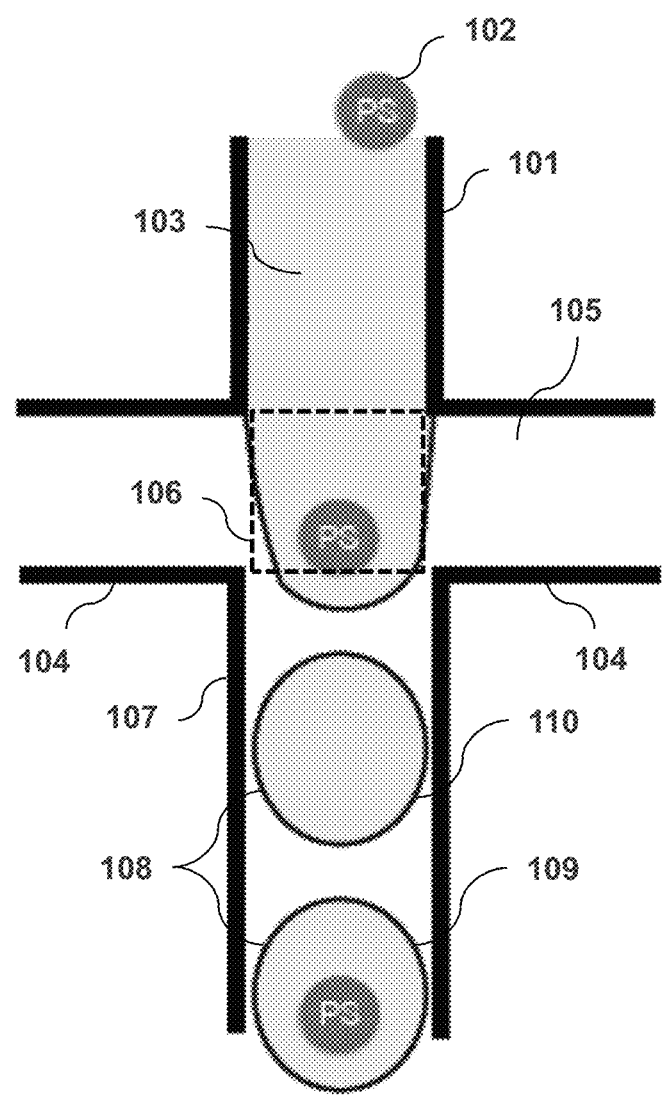
FIG. 1 shows a schematic of a particle encapsulation device used to generate a mixture of gel-coated particles and gel beads lacking the particles.

Unless defined otherwise, technical and scientific terms used herein have the same meaning as commonly understood by a person of ordinary skill in the art. Methods, devices, and materials similar or equivalent to those described herein can be used in the practice of this invention. The following definitions are provided to facilitate understanding of certain terms used frequently and are not meant to limit the scope of the present disclosure.

As used herein, the term "gel" refers to a dilute network of cross-linked material that exhibits no flow when in the steady-state. A "hydrogel" is a gel in which the liquid component of the gel is water. Gels and hydrogels can be deformable. Gels and hydrogels can be in a sol (liquid) or gel (solid) form. In some cases, hydrogels are reversible. Reversible hydrogels can be reversibly transitioned between a sol (liquid—also referred to herein as a "pre-gel") or gel (solid) form. For example, agarose hydrogel can be transitioned into a sol form with heat and a gel form with cooling. Alternatively, some hydrogel compositions exist in a sol form below a transition temperature and a gel form above the transition temperature. In some cases, a sol (liquid) hydrogel, or hydrogel precursor, can be irreversibly hardened into a gel form. For example, acrylamide can be irreversibly polymerized into a gel form. As used herein, sol refers to either the soluble form of a hydrogel, or soluble hydrogel precursor, and gel refers to a solid hydrogel. Numerous reversible and irreversible hydrogel compositions are known in the art, including those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and international Patent Publication Nos. WO/1997/030092; and WO/2001/049240.

As used herein, "oligonucleotide" means DNA, RNA, single-stranded, double-stranded, or more highly aggregated hybridization motifs, or any chemical modifications thereof. The oligonucleotide length can vary. In some embodiments, the oligonucleotide will be less than 500 nucleotides long, e.g., 2-500, 5-300, 4-100, 5-50 nucleotides long. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodouracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

The term "emulsion," refers to a mixture of two or more fluids that are immiscible. An emulsion can include a first phase in a second phase, such as an aqueous phase in an oil phase. In some cases, an emulsion includes more than two phases. Some embodiments also include multiple emulsions. Moreover, in some examples, an emulsion includes particulates that function to stabilize the emulsion and/or function as a coating (e.g., gel-like coating), such as a droplet skin.

The term "droplet" refers to a small volume of liquid, typically with a spherical shape, encapsulated by an immiscible fluid, such as a continuous phase or carrier liquid of an emulsion. In some embodiments, the volume of a droplet, and/or the average volume of droplets in an emulsion is, for example, less than about one microliter (ke., a "microdroplet") (or between about one microliter and one nanoliter or between about one microliter and one picoliter), less than about one nanoliter (or between about one nanoliter and one picoliter), or less than about one picoliter (or between about one picoliter and one femtoliter), among others. In some embodiments, a droplet (or droplets of an emulsion) has a diameter (or an average diameter) of less than about 1000, 100, or 10 micrometers, or of about 1000 to 10 micrometers, among others. A droplet can be spherical or nonspherical. A droplet can be a simple droplet or a compound droplet, that is, a droplet in which at least one droplet encapsulates at least one other droplet.

The droplets of an emulsion can have any uniform or non-uniform distribution in the continuous phase. If non-uniform, the concentration of the droplets can vary to provide one or more regions of higher droplet density and one or more regions of lower droplet density in the continuous phase. For example, droplets can sink or float in the continuous phase, can be clustered in one or more packets along a channel, can be focused toward the center or perimeter of a flow stream, or the like. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Any of the emulsions disclosed herein can be monodisperse, that is, composed of droplets of at least generally uniform size, or can be polydisperse, that is, composed of droplets of various sizes. If monodisperse, the droplets of the emulsion can, for example, vary in volume by a standard deviation that is less than about plus or minus 100%, 50%, 20%, 10%, 5%, 2%, or 1% of the average droplet volume. Droplets generated from an orifice similarly can be monodisperse or polydisperse.

The term "oil" refers to any liquid compound or mixture of liquid compounds that is immiscible with water and that has the majority of its molecular weight in the form of carbon. In some examples, oil also has a high content of hydrogen, fluorine, silicon, oxygen, or any combination thereof, among others. For example, any of the emulsions disclosed herein are in some embodiments a water-in-oil (W/O) emulsion (aqueous droplets in a continuous oil phase). In some embodiments, the oil is or includes at least one silicone oil, mineral oil, fluorocarbon oil, vegetable oil, or a combination thereof, among others.

Any other suitable components can be present in any of the emulsion phases, such as at least one surfactant, reagent, sample, other additive, label, particles, or any combination thereof. An emulsion can have any suitable composition. In some embodiments, the emulsion is characterized by the predominant liquid compound or type of liquid compound in each phase. In some embodiments, the predominant liquid compounds in the emulsion are water and oil. A method of generating a stabilized emulsion is provided. In some embodiments, the emulsion comprises droplets of the aqueous phase disposed in a nonaqueous continuous phase. In some embodiments, an emulsion is formed comprising droplets of the nonaqueous phase disposed in an aqueous continuous phase. In some embodiments, an interfacial skin is created between each droplet and the continuous phase, to transform the droplets into capsules. In some embodiments, the aqueous phase provided comprises skin-forming proteins and at least one surfactant. In some embodiments, the emulsion further comprises a spacing fluid that is miscible with the continuous phase and has a different composition than that of the continuous phase. Exemplary descriptions of emulsion formation methods can be found in U.S. Patent Application No. 2012/0152369, which is entirely incorporated herein by reference for all purposes.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

DETAILED DESCRIPTION OF THE INVENTION

The inventors have discovered a surprising route for achieving an enriched or uniform population of gel-coated particles in which one particle is contained in at least the majority of the isolated gel beads and there are few gel beads lacking particles. For example, in some embodiments, the resulting population of gel beads will not have a Poisson distribution of particles but instead will have proportionally more gel beads comprising a single particle and proportionally fewer gel beads lacking a particle than would be predicted from a Poisson distribution of particles in the gel beads. The methods, devices, and mixtures provided herein achieve this population by separating gel-coated particles from gel beads lacking a particle based on the difference between their buoyant densities.

Because the process of loading material into droplets is purely random, the distribution is dictated by Poisson statistics. Poisson statistics refers to a distribution of probability of a given number of events occurring in a fixed interval or time and/or space, if these events occur with a known average frequency that is independent of the previous occurrence of the event Poisson statistic can be used, for example, to calculate particle concentration distributions to evaluate the probability of clogging, as in Wyss H M, Blair D L, Morris J F, Stone H A, and Weitz D A, Mechanism for clogging of microchannels. Physical Review E 2006; 74: 61402. Poisson statistics can also be used, for example, to determine the distribution of material within a population of droplets, as in Abate A R, Chen C-H, Agresti, J J, and Weitz D A. Beating Poisson encapsulation statistics using close-packed ordering. Lab on a Chip 2009; 9: 2628-2631. Further exemplary descriptions of applying Poisson statistics are provided in WO 2010/036352, which is entirely incorporated herein by reference for all purposes.

According to Poisson statistics, the probability of a droplet containing, for example, k particles, is $\lambda^k \exp(-\lambda)/(k!)$, where $\lambda$ is the average number of particles per droplet. This means that to minimize the number of droplet containing multiple particles, one must reduce the average loading densities. An undesired side effect of this strategy is that a significant number of droplets will contain no particles whatsoever, reducing the percentage of droplets that are usable. The methods, devices, and mixtures described herein work to mitigate these issues by enabling the effective separation of desired droplets from those that are unusable.

The newly discovered method comprises providing a suspension of a plurality of particles to be partitioned within gel beads or droplets. In some embodiments, the particles comprise a rigid solid. The particles can comprise, for example, polymethylmethacrylate, glass, polystyrene, or one or more polymers compatible with solid-phase oligonucleotide synthesis. Particles can include, for example, controlled pore glass (CPG)(available from Glen Research, Sterling, Va.), oxalyl-controlled pore glass (See, e.g., Alul, et al., Nucleic Acids Research 1991, 19, 1527), TentaGel Support—an aminopolyethyleneglycol derivatized support (See, e.g., Wright, et al., Tetrahedron Letters 1993, 34, 3373), polystyrene, Poros—a copolymer of polystyrene/divinylbenzene, or reversibly cross-linked acrylamide. Many other solid supports are commercially available and amenable to the present methods. In some embodiments, the particles have a diameter in the range from about 0.1 μm to about 180 μm, from about 0.1 μm to about 120 μm, from about 0.1 μm to about 60 μm, from about 0.1 μm to about 30 μm, from about 1 μm to about 180 μm, from about 1 μm to about 120 μm, from about 1 μm to about 60 μm, from about 1 μm to about 30 μm, from about 10 μm to about 180 μm, from about 10 μm to about 120 μm, from about 10 μm to about 60 μm, from about 10 μm to about 30 μm, or from about 20 μm to about 40 μm.

The particles can comprise a material that responds to a magnetic field. The material can have paramagnetic, metamagnetic, ferromagnetic, or ferrimagnetic properties. The material can comprise, for example, a metal or a metal oxide. Example materials include iron, nickel, cobalt, $Fe_3O_4$, $BaFe_{12}O_{19}$, CoO, NiO, $Mn_2O_3$, $Cr_2O_3$, and CoMnP.

The particles are next coated with a gel. In some embodiments, this coating is applied with a particle encapsulation device. This particle encapsulation device can be, for example, a droplet generator. Many configurations of droplet generators may be suitable for coating the particles with a gel according to the present teachings. For example, suitable droplet generators include butted tubes, tubes drilled with intersecting channels, tubes partially or completely inserted inside other tubes, and tubes having multiple apertures, among others, where "tubes" means elongate hollow structures of any cross-sectional shape. Suitable fluid reservoirs include pipette tips, spin columns, wells (either individual or in a plate array), tubes, and syringes, among others. General principles of droplet generation and examples of droplet generators embodying those principles are described in WO 2011/120024, which is entirely incorporated herein by reference for all purposes. In some embodiments, the particles are coated through graft polymerization of a hydrogel off the surface of the particle.

The gel used to coat the particles can comprise, for example, polyacrylamide, agarose, agar, poly(lactic co-glycolic acid), or polyethylene glycol. Other hydrogels include, but are not limited to, those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and International Patent Publication Nos. WO/1997/030092; and WO/2001/049240. In some embodiments, the particles are first coated in gel that is in an aqueous pre-gel state (i.e., sol form). This pre-gel has not yet undergone crosslinking, or gelation, of the majority of its constituent component molecules. Droplets of gel or pre-gel that do not comprise any particles are referred to herein as gel beads lacking particles. In some embodiments, these gel beads have a diameter in the range from about 1 µm to about 300 µm, from about 1 µm to about 200 µm, from about 1 µm to about 100 µm, from about 1 µm to about 50 µm, from about 10 µm to about 300 µm, from about 10 µm to about 200 µm, from about 10 µm to about 100 µm, from about 10 µm to about 50 µm, from about 20 µm to about 300 µm, from about 20 µm to about 200 µm, from about 20 µm to about 100 µm, or from about 20 µm to about 50 µm.

The ratio of gel bead diameter (Dg) to particle diameter (Dp) can be selected to enhance a density-driven separation of those gel beads that do not comprise any particles from those gel beads that do comprise a particle. In some embodiments, the ratio of Dg/Dp is in the range from about 0.005 to about 3000, from about 0.01 to about 800, from about 0.02 to about 200 from about 0.05 to about 60, from about 0.1 to about 20, or from about 0.2 to about 5. In some embodiments, the ratio of Dg/Dp is from about 0.25 to about 5.

The coating step of the method generates a starting mixture that comprises gel beads containing a distribution of particles determined by Poisson statistics. According to the Poisson distribution for particular operating conditions of the device, the starting mixture can comprise a distribution of gel beads that contain 0, 1, 2, 3 or more particles. To increase the frequency of droplets that contain zero or one particle, the volume fraction of particles in the provided particle suspension can be lowered. In some embodiments, the volume fraction of particles in the provided particle suspension is in the range from 0 to about 0.5, from 0 to about 0.4, from 0 to about 0.3, from 0 to about 0.2, from 0 to about 0.1, from 0 to about 0.01, or from 0 to less than 0.01. In some embodiments, the frequency of droplets containing one particle is from about 5% to about 10%.

The starting mixture of the provided method is generated under conditions in which the proportion of gel beads containing two or more particles is small. For example, in some embodiments, the starting mixture will have no more than 5, 4, 3, 2, or 10% beads having two or more particles. Additionally, in some embodiments, the starting mixture comprises at least 1, 2, 3, 4, 5, 6, 7, 8, 9, 10, 11, 12, 13, 14, 15, 16, 17, 18, 19, 20, or more gel beads lacking particles for every gel-coated particle.

One embodiment of a particle encapsulation device is shown in FIG. 1. The schematic view depicts a center inlet channel 101 that comprises a suspension of particles 102 within a first fluid 103. The side inlet channels 104 comprise a second fluid 105 that is at least partially immiscible with the first fluid. The three channels carrying these inlet streams converge to form a nozzle 106. As the first fluid contacts the second fluid at the nozzle, and the combined mixture continues to flow through an outlet channel 107, an emulsion is formed comprising droplets 108. Some these droplets 109 can contain one particle. Other droplets 110 can contain no particles.

In some embodiments, the first fluid 103 is aqueous. In some embodiments, the second fluid 105 is an oil. In some embodiments, the second fluid comprises an oil and a surfactant.

The fluids can be moved through the device using one or more pumps. Each embodiment is compatible with any suitable method of pumping, including at least pressure-controlled pumping, vacuum-controlled pumping, centrifugation, gravity-driven flow, positive displacement pumping, syringe pumping, and peristaltic pumping.

The average volume of the droplets 108 can be varied by matching the size of the nozzle 106 to the desired drop diameter, and selecting appropriate flow rates of the first fluid 103 and second fluid 105 to operate the device in a dripping regime. In some embodiments, this entails controlling the activities of one or more pumps to regulate the flow rates of the first fluid 103 and the second fluid 105.

Clogging of microfluidic devices such as the one described herein occurs if a solid particle contacts a channel opening that is smaller in size than the diameter of the particle. Clogging can also occur even when the channel opening or interior is of a larger size than that of solid particles suspended in a fluid flowing through the device, if the volume fraction of the particles is sufficiently large. A mathematical model of a mechanism for the clogging of microchannels can be found in Wyss H M, Blair D L, Morris J F, Stone H A, and Weitz D A. Mechanism for clogging of microchannels. Physical Review E 2006; 74: 61402, which is entirely incorporated herein by reference for all purposes. The frequency of clogging of the inlet channel 101 can be reduced by increasing the channel diameter and length relative to that of the particles 102. In some embodiments, the inlet channel has a diameter of from about 1× to about 1000×, from about 1× to about 300×, from about 1× to about 100×, from about 1× to about 30×, from about 1× to about 10×, from about 1× to about 3×, or from about 1× to about 2× that of the particle diameter. In some embodiments, the inlet channel has a diameter of about 3× that of the particle diameter. In some embodiments, the inlet channel has a length of from about 1× to about 1000×, from about 1× to about 300×, from about 1× to about 100×, from about 1× to about 30×, from about 1× to about 10×, from about 1× to about 3×, or from about 1× to about 2× that of the particle diameter.

After generating the droplets 108 (some containing particles, some not), the starting mixture emulsion is collected.

In some embodiments, the droplets in the starting mixture are pre-gel (not solid gel) and are crosslinked to form gels after collection of the starting mixture.

In some embodiments, the starting population of gel beads (some containing particles, some not), is moved into an aqueous phase. The droplets in an emulsion also can be broken by diluting the surfactant in the oil or by centrifugation to pull the droplets into an aqueous solution. The density of the aqueous phase can be adjusted to affect the relative buoyancies of droplets containing different numbers of particles.

The method provided further comprises allowing the mixture of gel-coated particles and gel beads lacking the particle to be separated within a fluid. The separation is based on the presence and number of particles contained within the droplets. In one embodiment, the separation is between gel-coated particles (droplets containing one or more particle) and gel beads lacking the particle (droplets not containing a particle). In other embodiments, the separation is between droplets containing two or more particles, and droplets containing one or no particles. Other separations that can be accomplished with the method are between droplets containing three or more particles, and droplets containing two or fewer particles; between droplets containing four or more particles, and droplets containing three or fewer particles; between droplets containing five or more particles, and droplets containing four or fewer particles; between droplets containing six or more particles, and droplets containing five or fewer particles; between droplets containing seven or more particles, and droplets containing six or fewer particles; between droplets containing eight or more particles, and droplets containing seven or fewer particles; between droplets containing nine or more particles, and droplets containing eight or fewer particles; and between droplets containing ten or more particles, and droplets containing nine or fewer particles.

The separation can be caused by differences in buoyancy between droplets containing different numbers of particles. The separation can also be caused by different responses of droplets containing different numbers of particles to, for example, the presence of a magnetic field, an electrical field, or a fluid flow. In some embodiments, the separation is caused by differential settling of droplets containing different numbers of droplets based on resulting density differences of the droplets.

The fluid in which separation occurs can comprise a single liquid phase or a plurality of liquid phases. The fluid can comprise an aqueous solution. The fluid can be a mixture of an aqueous fluid and an oil. In some embodiments, the gel-coated particles have a higher density than that of the gel beads lacking the particles. In these embodiments, the density of the fluid can be selected such that the gel-coated particles settle at a lower level than that of the gel beads lacking the particle. In other embodiments, the gel-coated particles have a lower density than that of the gel beads lacking the particles. In these embodiments, the density of the fluid can be selected such that the gel-coated particles settle at a higher level than that of the gel beads lacking the particle. Settling based on differential density of empty gel beads and those containing particles can occur based on gravity or can be induced by mechanical force, e.g., centrifugation.

Separation based on buoyancy differences can occur based on settling as described above, or can occur dynamically. In some embodiments, the fluid that the separation occurs within has a higher density than that of the droplets in the starting mixture. In this case, all droplets will rise within the fluid. Those droplets having a lower density, because of differences in the number of contained particles, will rise more rapidly than those droplets having a higher density. In some embodiments, the fluid that the separation occurs within has a lower density than that of the droplets in the starting mixture. In this case, all droplets will sink within the fluid. Those droplets having a higher density, because of differences in the number of contained particles, will sink more rapidly than those droplets having a lower density.

Figure 2:
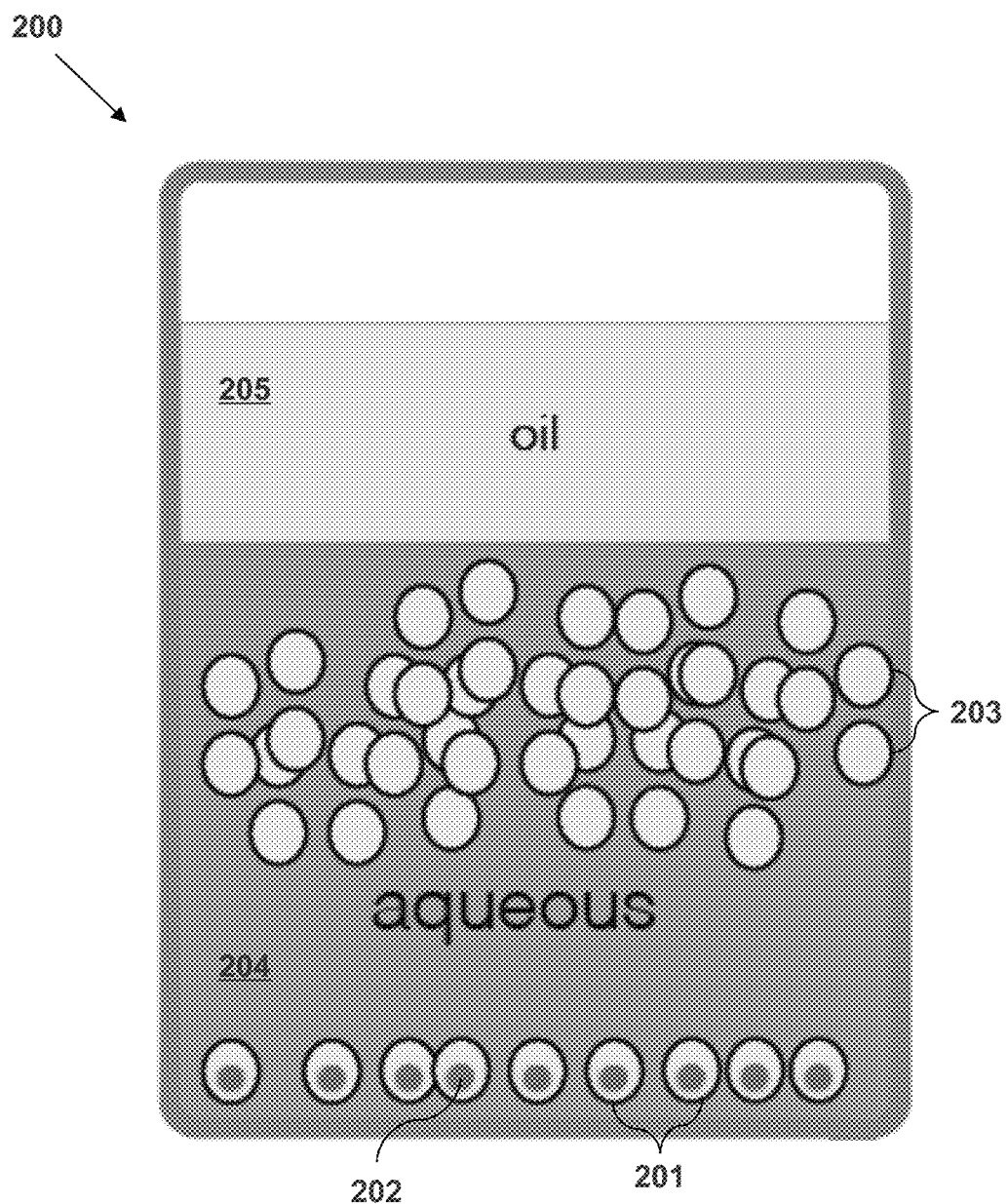
FIG. 2 shows a schematic of a separation device used to isolate an enriched population of gel-coated particles based on differences in the buoyant densities of gel-coated particles and gel beads lacking the particles.

FIG. 2 shows an exemplary device 200 for separating the droplets, gel-coated particles, or gel beads lacking particles, once formed. The droplets 201 that contain one particle will have a different buoyant density than the droplets 203 that do not contain a particle. In some embodiments, the droplets 201 that contain a particle have a lower density than the empty droplets 203. In the embodiment shown in FIG. 2, the droplets 201 that contain a particle have a higher density than those of the empty droplets 203. In some embodiments, the density of the particle 202 is greater than or equal to 1.01 g/cm3, 1.02 g/cm3, 1.03 g/cm3, 1.04 g/cm3, 1.05 g/cm3, 1.06 g/cm3, 1.07 g/cm3, 1.08 g/cm3, 1.09 g/cm3, 1.10 g/cm3, 1.20 g/cm3, 1.30 g/cm3, 1.40 g/cm3, or 1.50 g/cm3.

The droplets are suspended in a solution 204, after being moved from the second fluid 205 by, for example, centrifugation, gravitational displacement, pumping, or any other mechanism for movement within a fluid. The density of the solution 204 is controlled such that the empty droplets 203 will float, while the droplets 201 that contain a particle will sink. After the droplets have been thus separated, the population of droplets that contain particles can be isolated for further processes.

The method provided further comprises collecting the thus separated gel-coated particles such that a majority of the gel beads lacking the particle are not also collected. In this way the method produces an enriched collected population of gel-coated particles. In some embodiments, the collected population comprises at least 1, 2, 3, 4, 5, 6, 7, 8, 9, 10, 20, 30, 40, 50, 60, 70, 80, 90, 100, 200, 300, 400, 500, 600, 700, 800, 900, 1000, or more gel-coated particles for every gel bead lacking particles. Collection can comprise, for example, moving the gel beads containing particles into another vessel, thus physically separating the gel beads with particles from at least a majority of those lacking particles. The resulting collected mixture will be greatly enriched for gel beads containing particles. For example, in some embodiments, at least 90% of the gel beads will comprise one particle and less than 10% of the gel beads will lack a particle.

Once isolated, the enriched collected population of gel-coated particles can be passed through a second droplet generator to co-encapsulate the gel-coated particles into droplets at a high efficiency. In some embodiments of the method, the gel coating on the particles reduces the clogging of narrow channels in this second droplet generator. In general, as the volume fraction of particles is increased, the probability that a concentration fluctuation will be large enough to block a channel also increases. As a result, clogging is typically strongly correlated with the particle volume fraction value. By first coating the particles with a deformable gel, the method, devices, and mixtures provided herein instead allow for a higher volume fraction of particles to be employed in subsequent co-encapsulation, increasing the efficiency of droplet loading without negatively affecting the likelihood of clogging.

Figure 3:
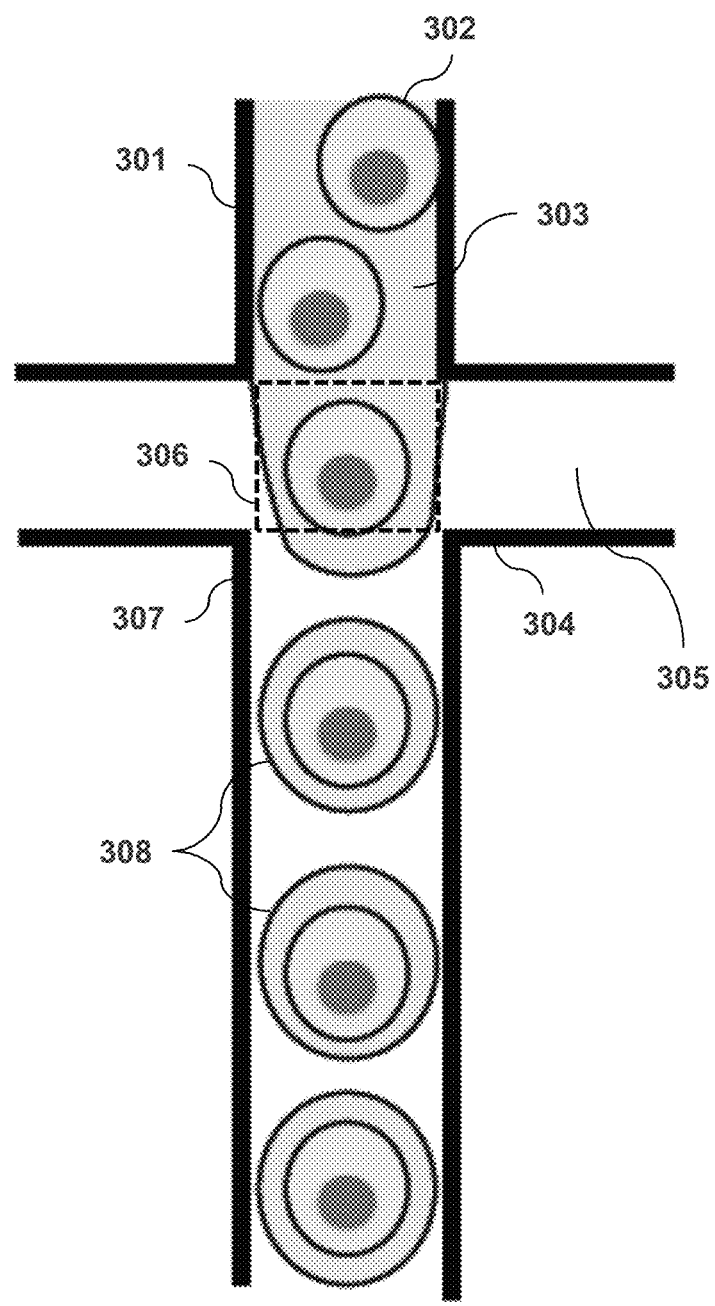
FIG. 3 shows a schematic of a droplet generating device used to produce a population of gel-coated particles co-encapsulated with droplets.

FIG. 3 shows one example of a droplet generator for co-encapsulating the gel-coated particles within droplets at high efficiency. In the device shown in the figure, a second center inlet channel 301 comprises a suspension of particle-containing droplets 302 within a third fluid 303. The second side inlet channels 304 comprise a fourth fluids 305. The three channels carrying these inlet streams converge to form a second nozzle 306. As the third fluid contacts the fourth fluid at the nozzle, and the combined mixture continues to flow through a second outlet channel 307, an emulsion is formed comprising secondary droplets 308.

In embodiments in which the droplets 302 are deformable gel-coated particles, the ability of the gel to deform allows the gel-coated particles to be packed at a volume fraction approaching 1.0 without clogging the second center inlet channel 301 or the second nozzle 306. This is in contrast to the lower particle volume fraction used in operating the first droplet generator of FIG. 1. The high volume fraction and close packing achievable with the deformable gel-coated particles enable them to order into a regular spacing, and to obtain uniform filling of the secondary droplets 308, such that each secondary droplet comprises a layer of the third fluid 303, a layer of the deformable gel, and a single particle.

In some embodiments, the third fluid 303 comprises materials to be co-encapsulated into the secondary droplet 308 along with the one particle. In some embodiments this co-encapsulated material comprises one or more cells. In some embodiments, the co-encapsulated material comprises another particle type. In some embodiments, the co-encapsulated material comprises one or more reaction substrates. In some embodiments, the co-encapsulated material comprises one or more reaction mixture components. The reaction mixture components can be, for example, DNA, RNA, oligonucleotides, nucleotides, enzymes, buffers, salts, or other components of molecular biology reactions. In some embodiments, the co-encapsulated material comprises one or more nutrients supporting cellular metabolism. In some embodiments the co-encapsulated material in a droplet is a single cell, nucleic acid from a single cell, or nucleic acid from a plurality of cells. In some embodiments, the co-encapsulated material comprises mixtures of nucleic acids and/or proteins.

The method may further comprise additional steps subsequent to generating the population of gel-coated particles or subsequent to generating co-encapsulated droplets. In some embodiments, the method further comprises droplet merging. In some embodiments, the method further comprises droplet splitting. In some embodiments, the method further comprises droplet detecting. In some embodiments, the method further comprises droplet sorting. In some embodiments, the method further comprises other assays of the droplet geometry, components, or other properties.

One or more of the gel, pre-gel, or particle can comprise or be attached to one or more of a variety of compounds. The compounds can comprise a fluorescent chemical such as a fluorophore, an antibody, an enzyme, or an oligonucleotide such as a DNA fragment.

In some embodiments, an oligonucleotide (e.g., comprising a barcode) is covalently linked to the hydrogel. Numerous methods for covalently linking an oligonucleotide to one or more hydrogel matrices are known in the art. As but one example, aldehyde derivatized agarose can be covalently linked to a 5'-amine group of a synthetic oligonucleotide. See, e.g., PCTUS2015/37525.

Each of a majority of particles can be attached to a different oligonucleotide molecule. In some embodiments, each of a majority of these different oligonucleotide molecules has a sequence that is different than that of the sequence of the other oligonucleotide molecules. In this way, the individual particles, and the droplets that contain them, can be identified by a barcoding technique as the sequences of the oligonucleotides they comprise are determined. See, e.g., PCI 2015/37525. Oligonucleotide particles, including, but not limited to, particles made by solid phase synthesis of oligonucleotides onto the particles (e.g., containing a molecular and/or cellular/particle barcode) can comprise a large number of oligonucleotides. For example, in some embodiments, 1,000; 10,000; 100,000; $1 \times 10^6$; $1 \times 10^7$, or more oligonucleotides are attached to such a particle. Additional compositions and methods for making and using non-hydrogel particles, such as barcoded particles, include those described in, e.g., Macosko et al., Cell. 2015 May 21; 161(5):1202-14.

As used herein a "barcode" is a short nucleotide sequence (e.g., at least about 2, 4, 6, 8, 10, 12 or more, e.g., 2-100, 4-50 nucleotides long) that identifies a molecule to which it is conjugated. Barcodes can be used, e.g., to identify molecules in a droplet. Such a droplet-specific barcode should be unique for that droplet as compared to barcodes present in other droplets. For example, droplets containing target RNA from single-cells can subject to reverse transcription conditions using primers that contain a different droplet-specific barcode sequence in each droplet, thus incorporating a copy of a unique "cellular barcode" into the reverse transcribed nucleic acids of each droplet. Thus, nucleic acid from each cell can be distinguished from nucleic acid of other cells due to the unique "cellular barcode." In some cases, the cellular barcode is provided by a "particle barcode" that is present on oligonucleotides conjugated to a particle, wherein the particle barcode is shared by (e.g., identical or substantially identical amongst) all, or substantially all, of the oligonucleotides conjugated to that particle. Thus, cellular and particle barcodes can be present in a droplet, attached to a particle, or bound to cellular nucleic acid as multiple copies of the same barcode sequence. Cellular or particle barcodes of the same sequence can be identified as deriving from the same cell, droplet, or particle. Such droplet-specific, cellular, or particle barcodes can be generated using a variety of methods, which methods result in the barcode conjugated to or incorporated into a solid or hydrogel support (e.g., a solid bead or particle or hydrogel bead or particle). In some cases, the droplet-specific, cellular, or particle barcode is generated using a split and mix (also referred to as split and pool) synthetic scheme as described herein. A droplet-specific barcode can be a cellular barcode and/or a particle barcode. Similarly, a cellular barcode can be a droplet specific barcode and/or a particle barcode. Additionally, a particle barcode can be a cellular barcode and/or a droplet-specific barcode.

In other cases, barcodes uniquely identify the molecule to which it is conjugated. For example, by performing reverse transcription using primers that each contain a unique "molecular barcode." In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 2:56 samples or less; a 6 nucleotide barcode can differentiate 4096 different samples or less; and an 8 nucleotide barcode can index 65,536 different samples or less. Additionally, barcodes can be attached to both strands either through barcoded primers for both first and second strand synthesis or through ligation.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N−1 deletions or other mutations from the canonical barcode sequence. Thus, barcodes that are referred to as "identical or substantially identical copies" refer to barcodes that differ due to one or more errors in, e.g., synthesis, polymerization, or purification and thus contain various N−1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from other barcodes of a population or different from barcodes of a different partition, cell, or bead). However, such minor variations from theoretically ideal barcodes do not interfere with the single cell analysis methods, compositions, and kits described herein. Therefore, as used herein, the term "unique" in the context of a particle, cellular, partition-specific, or molecular barcode encompasses various inadvertent N−1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research Can 11, (2010).

The provided method can further comprise the removal of the oligonucleotides from the gel-coated particle. In some embodiments, this removal is accomplished with enzymatic or chemical cleavage of covalent bonds. In some embodiments, the removed oligonucleotides diffuse away from the particles through the gel. In some embodiments, the gel is decomposed. In some embodiments, this decomposition is accomplished by melting the gel.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of generating a population of gel-coated particles, the method comprising,
    providing a plurality of particles;
    coating the particles with a gel to generate a starting mixture of gel-coated particles and gel beads lacking the particles, wherein the density of the gel-coated particles is higher than the density of the gel beads, and wherein the starting mixture generated by the coating has at least 10 gel beads lacking the particles per gel-coated particle;
    allowing the starting mixture to settle in a fluid such that a majority of the gel-coated particles separate in the fluid to a lower position than a majority of the gel beads; and
    collecting the gel-coated particles without a majority of the gel beads, thereby generating a collected population of gel-coated particles.

2. The method of claim 1, wherein oligonucleotides are linked to the particles.

3. The method of claim 2, wherein each of a majority of particles is attached to a different oligonucleotide, and the sequences of the different oligonucleotides are distinguishable from one another.

4. The method of claim 1, wherein the particles comprise one or more materials selected from the group consisting of polymethylmethacrylate, glass, and polystyrene.

5. The method of claim 1, wherein the gel is selected from the group consisting of polyacrylamide, agarose, agar, PLGA, polyethylene glycol, or alginate.

6. The method of claim 1, further comprising co-encapsulating gel-coated particles from the collected population of gel-coated particles into droplets.

7. The method of claim 1, wherein the fluid is a mixture of two immiscible fluids.

8. The method of claim 7, wherein the two immiscible fluids are an aqueous fluid and an oil.

9. The method of claim 1, wherein the particles have diameters in the range from about 1 µm to about 60 µm.

10. The method of claim 1, wherein the gel beads have diameters in the range from about 10 µm to about 100 µm.

11. A mixture of gel-coated particles and gel beads lacking the particles, wherein the mixture has been generated using the method of claim 1.

12. The mixture of claim 11, wherein oligonucleotides are linked to the particles.

13. The mixture of claim 12, wherein each of a majority of particles is attached to a different oligonucleotide, and the sequences of the different oligonucleotides are distinguishable from one another.

14. The mixture of claim 11, wherein the particles comprise polymethylmethacrylate, glass, polystyrene, or other polymers compatible with solid-phase oligonucleotide synthesis.

15. The mixture of claim 11, wherein the gel is selected from the group consisting of polyacrylamide, agarose, agar, PLGA, polyethylene glycol, or alginate.

16. The mixture of claim 11, wherein the particles have diameters in the range from about 1 µm to about 60 µm.

17. The mixture of claim 11, wherein the gel beads have diameters in the range from about 10 µm to about 100 µm.

* * * * *